United States Patent [19]

Malkoff

[11] Patent Number: 5,058,606
[45] Date of Patent: Oct. 22, 1991

[54] METHOD FOR SEALING EXTERNAL AUDITORY EAR CANAL

[76] Inventor: Jack Malkoff, 9810 N. 24th Pl., Phoenix, Ariz. 85028

[21] Appl. No.: 429,660

[22] Filed: Oct. 31, 1989

[51] Int. Cl.$^5$ .......................... A61F 11/08; A61F 11/12
[52] U.S. Cl. .................................... 128/864; 128/866; 2/209
[58] Field of Search ............... 128/864–867; 2/209, 68, 171, DIG. 11, 174

[56] References Cited

U.S. PATENT DOCUMENTS

| | | | |
|---|---|---|---|
| 1,648,608 | 11/1927 | Devlin | 2/68 X |
| 2,537,768 | 1/1951 | Laporte | 128/866 X |
| 2,738,514 | 3/1956 | Gondell | 2/68 X |
| 3,301,253 | 1/1967 | Glorig | 128/866 |
| 3,771,521 | 11/1973 | Kittredge | 128/864 |
| 3,881,570 | 5/1975 | Lewis | 128/864 X |
| 3,925,277 | 12/1975 | Lampe | 128/864 X |
| 4,023,642 | 5/1977 | Korn | 2/209 X |
| 4,160,449 | 7/1979 | Wade | 128/864 |
| 4,461,290 | 7/1984 | Gardner, Jr. et al. | 128/866 |
| 4,802,245 | 2/1989 | Miano | 2/209 |

FOREIGN PATENT DOCUMENTS

| | | | |
|---|---|---|---|
| 509686 | 8/1953 | Belgium | 128/866 |
| 2172508 | 9/1986 | United Kingdom | 128/865 |

*Primary Examiner*—Robert A. Hafer
*Assistant Examiner*—Kevin G. Rooney
*Attorney, Agent, or Firm*—Tod R. Nissle

[57] ABSTRACT

Apparatus for sealing the external auditory canal of an ear. The apparatus includes an ear protector band which extends over the forehead, ears, and nape of the head of an individual. The protector band prevents ear plugs from falling out of the ears of the individual, and tends to uniformly distribute compressive forces generated against the head by the band.

2 Claims, 1 Drawing Sheet

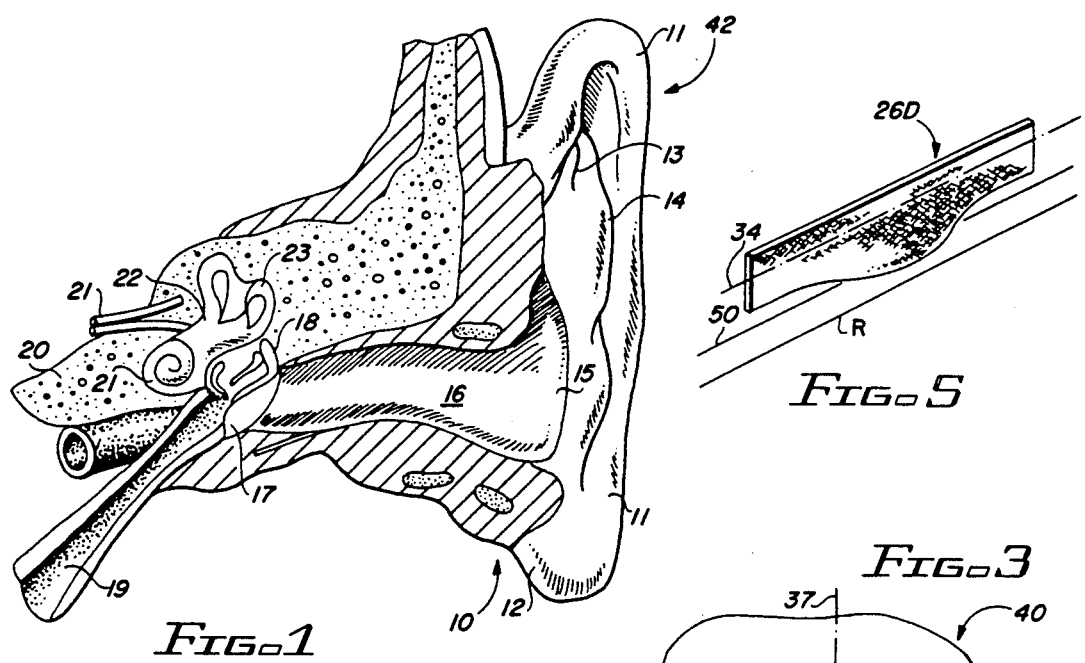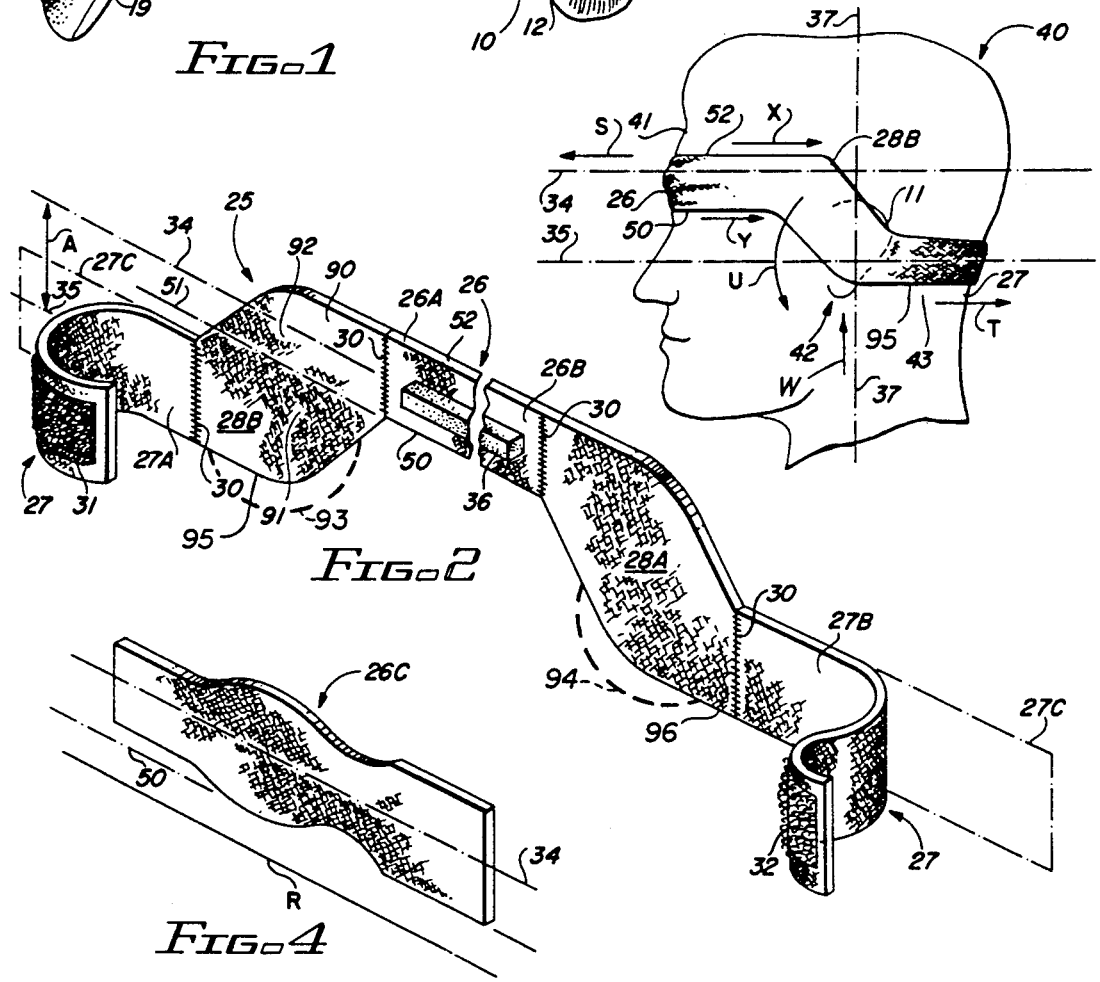

METHOD FOR SEALING EXTERNAL AUDITORY EAR CANAL

This invention relates to apparatus for preventing liquid from entering the external auditory canal of an individual's ear.

In a further respect, the invention relates to apparatus which seals the external auditory canal of an ear and which includes an ear protector band which extends over the forehead, ears, and nape of the head of an individual and produces generally uniform compressive forces at all points at which the band contacts the forehead.

In another respect, the invention relates to apparatus of the type described in which the portions of the band extending over the forehead and nape of the head of an individual are generally in parallel relationship and horizontally oriented to enable the band to be comfortably worn by an individual for extended periods of time.

Ear protector headbands are well known in the art. See, for example, U.S. Pat. Nos. 1,945,110 to Gordon, 2,070,216 to Rosenberg, and 2,738,514 to Gondell. Such conventional ear protector bands have a longitudinal axis which, when the band is worn about the head, circumscribes the head in ovoid fashion. Since the longitudinal axis or center line of a conventional headband lies in a plane, the headbands are worn in canted fashion, with the headband extending downwardly from the forehead over the ears and around the lower back of the head. When a headband is worn in canted fashion, the upper part of the section of the headband on the forehead tends to be pressed into the forehead with greater force than the lower part of the section of the headband on the forehead, making the headband uncomfortable to wear for extended periods of time.

Another disadvantage found in conventional ear protector bands is that they do not effectively prevent water from entering the ears of an individual. When an individual, particularly a child, has an ear infection or has a drainage tube inserted in the ear, it is imperative that water be prevented from entering the external auditory canal of the ear when the child is bathing or is swimming. U.S. Pat. No. 2,738,514 to Gondell describes a headband which purports to seal an ear by forcing protuberance 18 (FIG. 2 of the Gondell patent) against the ear tragus. Attempting to apply sufficient force to the tragus to seal the auditory canal causes discomfort to the tragus. This discomfort can be demonstrated to another by asking him to apply with his finger sufficient force to the tragus of his ear to tightly seal the auditory canal. The force applied to the tragus by the finger becomes uncomfortable in a short period of time. Finally, headbands like the Gondell headband ordinarily are not able to develop inward forces of a magnitude sufficient to seal the auditory canal by inwardly pressing the tragus of an ear.

Accordingly, it would be highly desirable to provide apparatus which could comfortably be worn on the head of an individual and which would effectively prevent water from entering the external auditory canal of an ear.

Therefore, it is a principal object of the invention to provide improved apparatus for preventing water from entering the external auditory canal of the ear of an individual.

Another object of the invention is to provide an improved ear protector headband which fits over the forehead and nape of the head of an individual and which presses against the forehead with a generally uniform force at all points at which the headband contacts the forehead of the individual.

A further object of the invention is to provide apparatus which prevents water from entering the external auditory canal of the ear and which includes a near protector band which only generates minimal, if any, forces against the tragus of the ears of an individual.

These and other, further and more specific objects and advantages of the invention will be apparent to those skilled in the art from the following detailed description therof, taken in conjunction with the drawings, in which:

FIG. 1 is a section view illustrating a human ear;

FIG. 2 is a perspective view of an ear protector headband constructed in accordance with the principles of the invention;

FIG. 3 is a side view of an individual wearing the headband of the invention to prevent liquid from penetrating the auditory canal of each ear;

FIG. 4 is a top perspective view illustrating an alternate construction of the forehead portion of the headband of the invention; and, FIG. 5 is a top perspective view illustrating another alternate construction of the forehead portion of the headband of the invention.

Briefly, in accordance with my invention, I provide improved headband apparatus for the head of an individual. The apparatus fits over the forehead, nape, and an ear of an individual. The ear includes an antihelix, a helix, a concha, a tympanic membrane, and an external auditory canal leading to the tympanic membrane The apparatus includes an earplug in the auditory canal of the ear, and includes an earplug retaining member circumscribing the head. The earplug retaining member includes a first upper elongate band extending across the forehead and having first and second ends; a patch portion which covers the auditory canal and at least a portion of the antihelix, helix and concha of the ear, which prevents the earplug from coming out of the auditory canal and falling free from the ear, and which is connected to the first end of the first band: a second lower elongate band extending around the nape of the head and having first and second ends, the first end connected to said patch portion; and, means for interconnecting said second ends of said first and second elongate bands. The first and second elongate bands each have a longitudinal axis and are attached to the patch portion in offset parallel relationship with the second band substantially beneath the first band and with the longitudinal axis of the second band beneath the longitudinal axis of the first band. The patch portion extends rearwardly intermediate and is subjected to shear forces by the first and second bands.

Turning now to the drawings, which depict the presently preferred embodiment and best mode of the invention for the purpose of illustrating the practice thereof, and not by way of limitation of the scope of the invention, and in which identical reference characters correspond to like elements throughout the several views, FIG. 1 illustrates a human ear including helix or outer rim 11 of the pinna 10, lobe 12, fossa 13 of the antihelix, antihelix 14, concha 15, external auditory canal 16, tympanic membrane 17, chain 18 of small bones in the middle ear, eustachian tube 19, temporal bone 20, auditory nerve 20, cochlea 21, vestibule 22, and semicircular canals 23. In the practice of the invention, a wax, rubber, plastic or other desired earplug is inserted in the auditory canal 16. The earplug is not, for the sake of clarity, drawn in the external auditory canal 16 in FIG. 1. The existence and use of such earplugs is well known in the art.

The earplug retaining member 25 of FIG. 2 includes first upper elongate band 26 which extends across the forehead of a user, patch portions 28A and 28B, and second elongate lower band 27 which, when member 25 is worn, extends around the nape of the head of an individual. Ends 27A and 27B of lower band 27 and ends 26A and 26B of upper band 26 are stitched 30 to patch portions 27 and 28 in the manner shown. Band 27 is cut in the middle and Velcro® pieces 31 and 32 secured to band 27 are detachably engaged with one another to mount member 25 around the head 40 as shown in FIG. 3. Dashed lines 27C represent band 27 when member 25 is laid on a flat surface and each portion of band 27 is laying on the surface in the same plane as band 26.

Band 26 has a longitudinal axis 34 which is spaced a distance A apart from the longitudinal axis 35 of band 27. Elongate soft foam or felt strip 36 is attached to the inside of band 26 to engage the skin on the forehead of an individual and help maintain member 25 in a desired position on the head of the user. In particular, strip 36 frictionally engages the skin and helps prevent member 25 from sliding around the head and around an imaginary vertical axis 37 through the center of the head.

In use, an earplug is inserted in the external auditory canal 16 of an ear to seal canal 16. A portion of the earplug may extend out of the canal from the concha 15 to or past the antihelix 14. The earplug, after being inserted in auditory canal 16 to seal canal 16, preferably extends outwardly from canal 16 a distance sufficient for patch portion 28B to contact the earplug when member 25 is placed around an individual's head 40 in the manner illustrated in FIG. 3. While the earplug need not contact patch portion 28B, the earplug typically tends better to stay in position in auditory canal 16 when it is at least lightly contacted by patch portion 28B.

Member 25 can be made from any desired material, but is presently preferably fabricated from an elastic fabric material. Member 25 is snugly secured about the forehead 41, ear 42, and nape 43 of the head 40. Bands 26 and 27 generate opposing shear forces S and T on patch portion 28B. Since bands 26 and 27 are vertically offset from and generally parallel to one another, bands 26 and 27 appear to function to more evenly distribute over the forehead 41 and nape 43 compressive forces generated against head 40 by member 25. Further, when conventional headbands like the band in U.S. Pat. No. 1,945,110 to Gordon are utilized, they often must be secured about the head in relatively tight manner to prevent the band from sliding down the head. The offset relationship of the bands 26 and 27 of the invention appears to require that member 25 be less tightly secured about the head 40.

In FIGS. 2 and 3, band 27 is secured to patch portions 28A and 28B below band 26, i.e., band 27 is secured to patch portions 28A and 28B at points below a horizontal line passing through the bottom edge 50 of band 26. While in FIGS. 2 and 3, band 27 is completely offset (i.e., is completely below) band 26, in the practice of the invention at least 50%, preferably 75% or more, of band 27 is beneath band 26 when the member 25 is laid on a flat surface in the manner described in FIG. 2. Band 27 is defined as being substantially below band 26 when shear forces S and T are generated on a patch portion 28A, 28B. Forces S and T produce a resultant rotational force U on a patch portions 28A and 28B.

Member 25 can be fabricated by cutting member 25 from a single piece of material, in which case ends 27A, 27B, 26A and 26B are integrally formed with or connected to one of patch portions 28A and 28B.

FIGS. 4 and 5 illustrate alternate embodiments 26C and 26D of band 26 and further illustrate how, when the bottom edge of band 26 is not straight, the bottom edge 50 is defined as the average elevation of the points along the bottom edge with respect to a reference line R.

In FIG. 3, shear forces S and T produce a resultant rotational torque tending to rotate patch portion 28B in the direction of arrow U. When patch 28B is fabricated from elastic fabric, the upper 90 and lower 91 portions of patch 28B tend to stretch more than the intermediate portion 92 of patch 28B. Portions 90 and 91 also tend to rotate about portion 92. This rotation tends to occur even if patch 28B is fabricated from metal or another non-elastic material. The stretching and/or rotation of patch 28B tends to make the force pulling on upper edge 52 equivalent to the force acting on lower edge 50 and tends to make the compressive forces generated against forehead 41 by band 52 more equivalent at all points.

Fur, down, or other material may be attached to the inner surfaces of patches 28B and 28A. Such fur, down or other material would, when the member 25 is worn about the head as shown in FIG. 3, contact and keep warm the portion of the helix 11 and antihelix 14 contacted by patch 28A, 28B. Patches 28A and 28B can each be made large enough to entirely cover the helix 11 and antihelix 14, etc. of an ear.

In the prior art a variety of ear covers exist which include ear plug portions directly attached to the ear cover. These prior art devices are not readily adapted to fit ears of varying shape and dimension and do not permit the ear plug portions to be laterally displaced while maintaining a seal of the auditory canal 16 and while maintaining the comfort of the user. For example, in U.S. Pat. No. 4,023,642 to Korn, the earplug 60 is attached to foam 50. The earcover housing or shell 40 and the earplug 60 are not intended to be laterally displaced on the user's head. If, in FIG. 2 of Korn, the earcover is slid upwardly toward the top of the user's head, the earplug is first uncomfortably canted in and then pulled from the user's auditory canal 70. The auditory canal is sensitive. Too much pressure in the auditory ear canal can quickly become uncomfortable to a user. This means that for a device like that shown in the Korn patent to be comfortable it has to be carefully fitted to the ear of the individual, which makes mass production of such an item difficult. Sizing an earplug to fit the individual is advisable because the size of the auditory canal 70, the size of the ear lobes, the size of the tragus, the point at which the auditory canal opens with respect to the size of the head, etc. can widely vary depending on age, race, set and an individual's genetic makeup. The shape and curvature of the portion of the skull surrounding the ear also varies. Consequently, insuring that the ear protection device in the Miano patent (U.S. Pat. No. 4,802,245) will seal an individual's ear is typically not a simple matter. Each cup-like member utilized in the Miano patent must be carefully fit over the ear, and be sized to fit an individual. Even then, the lateral displacement of the cup-like member of the Miano ear protector can negate the water proof seal between the cup and the head.

The bathing cap disclosed in U.S. Pat. No. 1,648,608 to Devlin suffers from the disadvantages described above for the Korn and Miano patents. The Devlin bathing cap cannot be made in a single size which will comfortably fit in a group of people chosen at random. The shape and dimension of individual's ears varies too widely. Further, any pulling force exerted on the bathing cap which is generally parallel to the side of the head and laterally pulls on an earplug can cause significant discomfort to the user. Such discomfort is especially noticeable when posts 14 in the Devlin device are skewed in and press against the ear canal. Lateral forces on a bathing cap or headband are common, especially during water polo or when children are pushing and playing in water. In such circumstances, the posts 14 in the Devlin bathing cap are particularly undesirable because they can bruise or injure the ear canal.

The ear protector in the Gondell patent also appears to be impractical because of the necessity of carefully fitting it to an individual's ears. Further, the claimed action of protuberance 18 (Col. 2, lines 32 and 33) against the tragus of the ear rapidly becomes very uncomfortable. This can be easily demonstrated by having an individual press down on his tragus (the flap of ear extending over the ear canal) an amount sufficient to seal the ear canal. The pressure applied to the tragus quickly becomes uncomfortable.

Two of the important virtues of the headband—earplug combination of the invention are first that the lateral displacement of the headband does not cause discomfort to the user or present the possibility that the inner ear canal will be injured, and second that the headband—earplug of the invention fits and can be readily worn by a great variety of people, i.e., the headband—earplug combination of the invention does not require that it be specially sized to fit each individual utilizing the invention.

In the presently preferred embodiment of the invention, soft pliable silicone is obtained and rolled into a ball. The ball is typically about 0.75 inches in diameter. The ball is placed inside the auricle of the ear over the auditory canal 16 and is gently pressed against the auricle. Pressing the pliable silicone ball causes it to gently penetrate a short distance into the auditory canal 16, and importantly, to spread laterally over the auricle away from the auditory canal and to spread laterally against the tragus. Consequently, the major function of the silicone ball in the method of the invention is to extend laterally sealingly away from the and cover the auditory canal 16. The elastic earplug retaining member 25 is then placed around the head in the manner illustrated in FIG. 3. Elastic patch portion 28B covers ear 42 and presses the auricle, including rim 11, toward the side of the head. Patch portion 28B also presses the tragus and silicone ear plug (i.e., the flattened silicone ball) against one another. Ordinarily the patch 28B contacts the tragus and gently presses it against the silicone ball. When the tragus is pressed against the silicone earplug, the tragus is only moved a short distance from its normal position in the ear. The earplug actually helps support the tragus in an upright outward orientation. Patch portion 28B may or may not directly contact the flattened pliable silicone earplug. If the patch portion 28B does not directly contact the silicone earplug, portion 28B is normally spaced only a relatively short distance, one-eighth of an inch or less, away from the silicone earplug; the distance between the patch portion 28B and earplug is preferably one-sixteenth of an inch or less. An important feature of the invention is that when patch 28B is laterally displaced over the side of the head in directions parallel to the side of the head and face, patch 28B can slidably move over the earplug. This "floating" earplug arrangement of the invention is crucial because even when the headband is sliding over the earplug, the pressure against the tragus and/or earplug is maintained and the earplug stays in position over the auditory canal without being significantly laterally displaced in the canal. This minimizes the likelihood of injury and greatly enhances the comfort of the apparatus of the invention. The patch portion 28B need not contact the silicone earplug because the earplug can, without losing its seal, move outwardly a small distance to contact the patch portion 28B. Contraction of the auditory canal during chewing or small lateral displacement of the silicone plug during sliding movement of patch portion 28B over the plug, can cause the pliable plug to be squeezed or outwardly displaced against and contact patch portion 28B. This ability of the flattened silicone plug to at certain times be free from contact with the patch portion 28B further demonstrates the "free floating" method and apparatus of the invention. The prior art, in contrast to my invention, teaches that a headband or strap must continually contact and press against an earplug.

Another advantage of the retaining member 25 utilized in the invention is that patch portions 28A and 28B of member 25 do not include sections 93 or 94 extending downwardly past the lower edges 95 or 96 of the member 25. When sections 93 and 94 extend below lower edges 95 or 96, then the shear force T does not effectively maintain the lower portion of patch 28B against the head. In particular, if the user jumps in a swimming pool, the upward force of water acting in the direction of arrow W (FIG. 3) more readily raises section 94 and permits water to penetrate intermediate patch 28B and the head and ear of the user. Consequently, it is preferred that member 25 not include sections 93 or 94 extending beneath edges 95 or 96. The headband in the Miano reference (U.S. Pat. No. 4,802,245) teaches away from this feature of the invention. Note the lower portions of the ear covering areas of the Miano headband.

Having described my invention in such terms as to enable those skilled in the art to understand and practice it, and having identified the presently preferred embodiments thereof:

I claim:

1. A method for preventing water from entering the ear of an individual, said ear including an auricle, a tympanic membrane, and an external auditory canal leading to the tympanic membrane, said auricle including an outer rim and a tragus, said tragus having a normal upright position in said ear adjacent said auditory canal, said method comprising:

(a) rolling a soft pliable silicone plug into a ball having a diameter of about three quarters of an inch;

(b) placing said silicone ball in the ear over the external auditory canal;

(c) gently pressing said silicone ball against the ear to force a portion of said silicone ball a short distance into said auditory canal and to flatten and laterally sealingly spread said ball against the auricle away from the auditory canal and against the tragus, said lateral spreading of said ball covering and sealing the auditory canal, said flattened silicone plug supporting said tragus in said normal upright position;
(d) placing an earplug retaining member around the head of the individual, said member including
  (i) a first upper elongate band extending across the forehead of the individual and having first and second ends,
  (ii) a pliable patch portion
    extending over said auditory canal and said tragus and at least a portion of the rim of the auricle of the ear,
    contacting and pressing the tragus against the flattened silicone plug,
    slidably contacting the silicone plug, and connected to said first end of said first band,
  (iii) a second lower elongate band extending around the nape of the head and having first and second ends, said first end of said second band being connected to said patch portion, and
  (iv) means for interconnecting said second ends of said first and second elongate bands;
  said patch portion, when laterally displaced over the ear in a direction of travel generally parallel to the head, sliding over said silicone plug while maintaining said flattened silicone plug in sealing contact with said auricle of said ear.

2. A method for preventing water from entering the ear of an individual, said ear including an auricle, a tympanic membrane, and an external auditory canal leading to the tympanic membrane, said auricle including an outer rim and a tragus, said tragus having a normal upright position in said ear adjacent said auditory canal said tragus having a normal upright position in said ear adjacent said auditory canal, said method comprising:
  (a) rolling a soft pliable silicone plug into a ball having a diameter of about three quarters of an inch;
  (b) placing said silicone ball in the ear over the external auditory canal;
  (c) gently pressing said silicone ball against the ear to force a portion of said silicone ball a short distance into said auditory canal and to flatten and laterally sealingly spread said ball against the auricle away from the auditory canal and against the tragus, said lateral spreading of said ball covering the auditory canal, said flattened silicone plug supporting said tragus in said normal upright position;
  (d) placing an earplug retaining member around the head of the individual, said member including
    (i) a first upper elongate band extending across the forehead of the individual and having first and second ends,
    (ii) a pliable patch portion
      extending over said auditory canal and said tragus and at least a portion of the rim of the auricle of the ear,
      contacting and pressing the tragus against the flattened silicone plug,
      slidably contacting the silicone plug, and connected to said first end of said first band,
    (iii) a second lower elongate band extending around the nape of the head and having first and second ends, said first end of said second band being connected to said patch portion, and
    (iv) means for interconnecting said second ends of said first and second elongate bands;
  said first and second elongate bands each being attached to said portion in offset parallel relationship with said second band substantially beneath said first band;
  each patch portion extending rearwardly intermediate and being subjected to shear forces by said first and second bands, said shear forces producing a resultant rotational torque acting on said patch portion; and,
  said patch portion, when laterally displaced over the ear in a direction of travel generally parallel to the head, sliding over said silicone plug while maintaining said flattened silicone plug in sealing contact with said auricle of said ear.

* * * * *